(12) United States Patent
Young

(10) Patent No.: US 8,414,575 B2
(45) Date of Patent: *Apr. 9, 2013

(54) LOW PROFILE RADIOFREQUENCY ELECTRODE ARRAY

(75) Inventor: Kimbolt Young, Newtonville, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1388 days.

This patent is subject to a terminal disclaimer.

(21) Appl. No.: 12/106,981

(22) Filed: Apr. 21, 2008

(65) Prior Publication Data

US 2008/0228182 A1 Sep. 18, 2008

Related U.S. Application Data

(63) Continuation of application No. 11/132,754, filed on May 18, 2005, now Pat. No. 7,371,234.

(51) Int. Cl.
*A61B 18/14* (2006.01)

(52) U.S. Cl. .......................................... 606/41; 607/115

(58) Field of Classification Search ............... 606/32, 606/41, 46–48, 50; 600/393; 607/98, 99, 607/115, 128
See application file for complete search history.

(56) References Cited

U.S. PATENT DOCUMENTS

| | | | |
|---|---|---|---|
| 5,551,426 A * | 9/1996 | Hummel et al. | 600/374 |
| 5,672,173 A | 9/1997 | Gough et al. | |
| 5,827,276 A * | 10/1998 | LeVeen et al. | 606/41 |
| 6,379,353 B1 * | 4/2002 | Nichols | 606/41 |
| 6,468,273 B1 | 10/2002 | LeVeen et al. | |
| 6,780,180 B1 | 8/2004 | Goble et al. | |
| 7,195,629 B2 | 3/2007 | Behl et al. | |
| 7,371,234 B2 * | 5/2008 | Young | 606/41 |
| 2004/0181215 A1 * | 9/2004 | Kelly et al. | 606/41 |

OTHER PUBLICATIONS

PCT International Search Report for PCT/US2006/018874, Applicant: Boston Scientific Scimed, Inc., Form PCT/ISA/210 and 220, dated Oct. 10, 2006 (5 pages).
PCT Written Opinion for PCT/US2006/018874, Applicant: Boston Scientific Scimed, Inc., Form PCT/ISA/237, dated Oct. 10, 2006 (4 pages).
PCT International Preliminary Report on Patentability (Chapter I of the Patent Cooperation Treaty) for PCT/US2006/018874, Applicant: Boston Scientific Scimed, Inc., Form PCT/IB/326 and 373, dated Nov. 29, 2007 (6pages).
EPO Communication dated May 19, 2009 for European Patent Application No. 06 759 909.2-2305 (2 pages).

* cited by examiner

*Primary Examiner* — Michael Peffley
*Assistant Examiner* — Thomas Giuliani
(74) *Attorney, Agent, or Firm* — Vista IP Law Group LLP

(57) ABSTRACT

An electrosurgical device for tissue ablation includes a delivery cannula having a lumen and an open distal end in communication with the lumen, wherein an electrode array comprising a plurality of tines is deployable from, and retractable into, the cannula lumen through the open distal end. The electrode array tines have proximal ends secured to a mandrel carried in the cannula lumen, the mandrel being movable axially relative to the cannula, wherein the tines, when the electrode array is retracted into the cannula lumen, are nested in offset, circumferential layers about the mandrel.

19 Claims, 2 Drawing Sheets

LOW PROFILE RADIOFREQUENCY ELECTRODE ARRAY

RELATED APPLICATION DATA

This application is a continuation application of U.S. Patent Application Serial No. 11/132,754, filed May 18, 2005, now issued as U.S. Pat. No. 7,371,234, the contents of which are incorporated herein by reference as though set forth in full.

FIELD OF THE INVENTION

The present invention relates generally to medical devices for treating tumors and, more specifically, to devices for treating tumors using radiofrequency energy.

BACKGROUND OF THE INVENTION

Known radiofrequency ("RF") ablation devices employ an array of electrode tines deployed from the end of a single delivery cannula to transmit RF energy into a targeted tissue area, e.g., a tumor, causing heating and eventual ablation of the tissue area. Such electrode array devices include the LeVeen Needle and Co-Access (collectively "LeVeen Needle") devices manufactured and distributed by Boston Scientific Corporation. The actual number of tines provided on the various electrode array devices, including but not limited to the LeVeen Needle devices, depends in part on the size of the tissue area to be ablated. There are natural limitations on the effective cross-sectional area that any single tine can contribute to the overall ablation, typically about 1 cm in diameter. Thus, for creating larger ablation areas, more tines are generally needed. Of course, since all of the tines must be able to be housed in the delivery cannula, the greater the number of tines, the greater the delivery cannula profile and attendant collateral tissue damage caused by larger gauge cannula.

SUMMARY OF THE INVENTION

In one embodiment, an electrosurgical device for tissue ablation includes a delivery cannula having a lumen and an open distal end in communication with the lumen. An electrode array comprising a plurality of tines is deployable from, and retractable into, the cannula lumen through the open distal end. The tines have proximal ends secured to a mandrel carried in the cannula lumen, the mandrel being movable axially relative to the cannula, wherein the tines, when the electrode array is retracted into the cannula lumen, are nested in offset, circumferential layers about the mandrel.

In another embodiment, an electrosurgical device for tissue ablation includes a delivery cannula having a lumen and an open distal end in communication with the lumen. An electrode array comprising a plurality of tines is deployable from, and retractable into, the cannula lumen through the open distal end. The tines have proximal ends secured to a mandrel carried in the cannula lumen, the mandrel being movable axially relative to the cannula, wherein the tines, when the electrode array is retracted into the cannula lumen, are nested in first and second circumferential layers about the mandrel, the first and second tine layers having a collective radial thickness less than twice a maximum radial thickness of any one tine.

In yet another embodiment, an electrosurgical device for tissue ablation includes a delivery cannula having a lumen and an open distal end in communication with the lumen. An electrode array comprising a plurality of tines is deployable from, and retractable into, the cannula lumen through the open distal end. The tines have proximal ends secured to a mandrel carried in the cannula lumen, the mandrel being movable axially relative to the cannula, wherein the tines, when the electrode array is retracted into the cannula lumen, are nested in first and second circumferential layers about the mandrel, wherein the tines in the second layer are supported by respective edges of adjacent tines in the first layer, and wherein the first and second layers have a collective radial thickness less than twice a maximum radial thickness of any one tine.

BRIEF DESCRIPTION OF THE DRAWINGS

Various embodiments of the invention are disclosed in the following detailed description, and in the accompanying drawings, in which.

DETAILED DESCRIPTION OF THE ILLUSTRATED EMBODIMENTS

Figure 1:
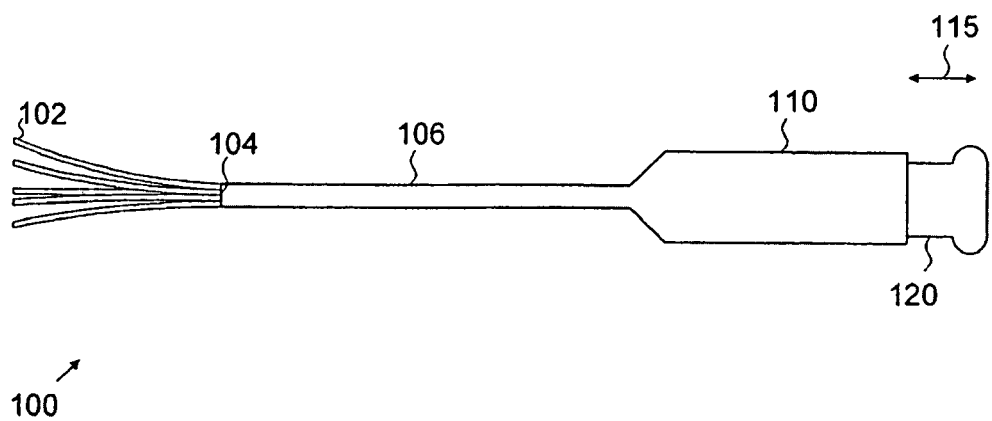
FIG. 1 is a perspective side view of an exemplary electrosurgical device, including an array of electrode tines extending from a distal end opening of the cannula.

FIG. 1 illustrates an exemplary electrosurgical device 100. Those knowledgeable in the art will recognize the device as being similar to LeVeen Needle and CoAccess (collectively "LeVeen") tumor ablation products manufactured and distributed by Boston Scientific Corporation. The device 100 generally includes an elongated cylindrical delivery cannula 106 attached to a proximal handle 110. An array of electrode tines 102 are extendable from, and retractable back into, an open distal end 104 of the cannula 106.

The proximal ends of the electrode tines 102 are secured to a distal end of an electrically conductive cylindrical mandrel (not shown) carried within, and axially movably relative to, the lumen of the cannula 106. A proximal end of the mandrel is fixed to a plunger 120 coupled in a reciprocating fashion to the handle 110, indicated by the two-directional arrow 115, such that extension and retraction of the electrode tines 102 from the cannula opening 104 is controlled by movement of the plunger 120 relative to the handle 110. The electrode tines 102 are biased such that, when the plunger 120 is depressed into the handle 110, the tines 102 are pushed outwardly, extending axially and radially from the cannula opening 104. When the plunger 120 is extended proximal to the handle 110, the tines 102 are withdrawn into the cannula 106, nesting circumferentially around the pusher mandrel in a linear configuration aligned axially with the cannula 106.

For use in a medical procedure, the distal end opening 104 of the cannula 106 is positioned proximate a target tissue mass, e.g., a cancerous tumor, in a patient. The distal tip of the cannula 106 may be sharpened so as to be tissue penetrating, allowing the attending physician to insert the cannula 106 directly through the patient's skin and intervening solid tissue. Alternatively, the cannula 106 may be inserted through the lumen of a previously positioned obtuator. Once in position at the target tissue site, the electrode tines 102 are deployed from the cannula opening 104, tracking through solid tissue and at least partially enveloping the tissue mass.

The proximal end of the plunger 120 includes an electrical connection (not shown) for coupling the mandrel and, thus, the electrode tines 102 to a radio frequency (RF) power generator (also not shown). The electrode tine array 102 acts as a first pole of a circuit powered by the generator, which is completed by a return "pad" electrode (not shown) secured to the patient's skin. The above-mentioned LeVeen products are operated in "monopolar" mode, which is to say, virtually all of the energy absorbed by the tissue is delivered in the tissue proximate the electrode array tines 102, causing tissue necrosis (or "ablation") of the target tissue mass. In other devices, a "bi-polar" mode operation is possible, wherein the ablation energy is distributed approximately evenly between respective electrode elements disposed in the target tissue mass.

As of the filing date of the present patent, the number of electrode tines in the array of commercially available LeVeen products varies with the size of the device. For example, a relatively large profile devices may have a dozen (or more) electrode tines. As will be appreciated, and with reference again to the exemplary device 100, the greater the number of individual electrode tines 102, the greater the circumferential profile of the cannula 106. This is because the proximal ends of the respective tines must all be accommodated on the mandrel; thus, the more tines, the greater the circumference (and diameter) of the mandrel.

Figure 2:
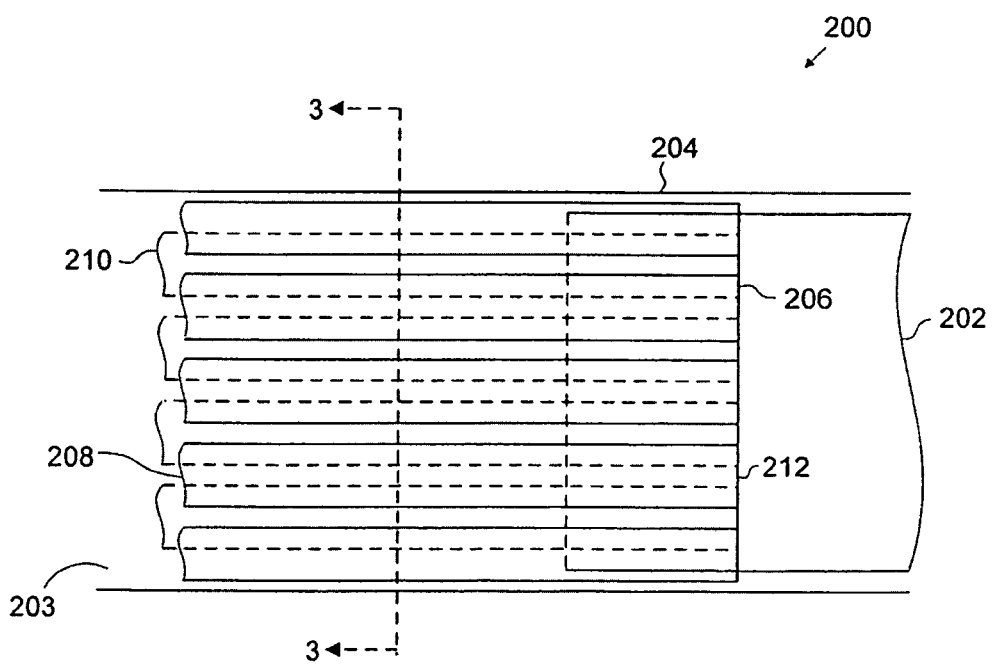
FIG. 2 is a cut-away side view of a distal end of an electrosurgical device according to one embodiment of the invention, showing the proximal ends of an array of electrode tines secured in overlapping layers to a pusher mandrel carried in the device.

Referring to FIG. 2, in one embodiment of the present invention, an electrosurgical device 200 is provided with a relatively greater number of electrode tines accommodated on a relatively smaller circumference mandrel 202 carried in the lumen 203 of a delivery cannula 204 by attaching the tines in overlapping, offset layers around the outer circumference of the mandrel 202. In particular, the device 200 includes a first ("inner") layer of electrode tines 210 having respective proximal ends 206 attached to, and displaced circumferentially around, the mandrel 202. The device 200 further includes a second ("outer") layer of electrode tines 208 having respective proximal ends 212 attached to, and displaced circumferentially around, the mandrel 202, with the respective outer tines 208 being centered approximately evenly between a pair of adjoining inner tines 210. It should be appreciated that, while two overlapping layers of electrode tines are shown in the embodiment of FIG. 2, in alternate embodiments, three or more overlapping layers of electrode tines may be employed.

Both the outer and inner electrode tines 208 and 210 may be secured to the mandrel 202 using various, well-known techniques. For example, the respective proximal ends 206 and 212 of the inner and outer tines 210 and 208 may be soldered (or spot-welded) to the mandrel 202. By way of another, non-limiting example, a glue or other adhesive may be used to attach the respective electrode tines 210 and 208 to the mandrel 202. By way of yet another, non-limiting example, the inner electrode tines 210 may be formed (i.e., laser cut) from the same tubular element forming the mandrel 202, with the out electrode tines 208 secured by solder weld or adhesive. In some embodiments, seams running between respective outer and inner tines 208 and 210 are laser welded, along with a butt weld around the stem of each tine, to provide sufficient tensile strength to prevent tines from breaking from the mandrel 202 during use. In one embodiment, the tines in the outer layer 208 extend proximally beyond the tines of the inner layer 210, so that the proximal ends of the respective tines may be secured to the mandrel 202 in a uniform manner.

Figure 3:
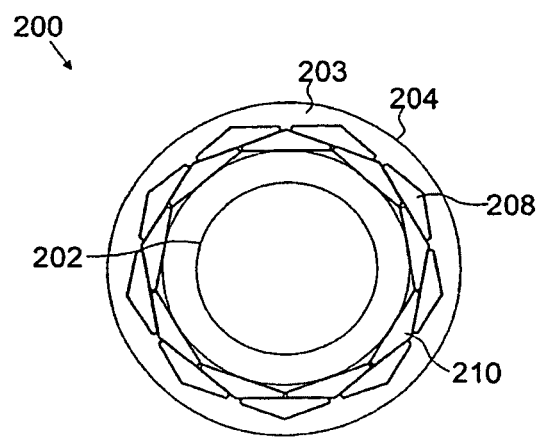
FIG. 3 is a cross-sectional end view taken across line 3-3 in FIG. 2, with the array of electrode tines being withdrawn in a nested configuration of offset-circumferential layers inside the cannula.

As best seen in FIG. 3, the outer electrode tines 208 are nested in an offset, circumferential layer above the inner electrode tines 210. In the illustrated device 200, the individual tine elements of the outer and inner electrode tine layers 208 and 210 have substantially uniform cross-sectional dimensions and patterns, which provide for a relatively low profile nesting of the respective inner and outer tine layers 210 and 208 when the tines are withdrawn into the lumen 203 of the cannula 204.

Figure 4:
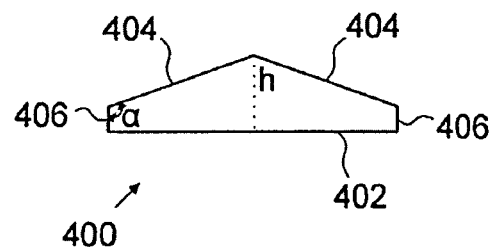
FIG. 4 is a cross-sectional view of an electrode tine in the device of FIG. 2.

As best seen in FIG. 4, each electrode tine (designated "400") of the offset layers 208 and 210 has a "A-frame" shape, including a substantially flat base 402. First and second sides 406 extend from opposing ends of, and generally perpendicular to, the base 402. First and second shoulders 404 extend at a substantially identical angle a from respective ends of the first and second sides 406, wherein the shoulders 404 meet at a maximum "radial height" h of the tine 400. As used herein with respect to the illustrated device 200, the radial height h of the tine 400 is measured from the intersecting point of shoulders 404 along a line that is substantially orthogonal to the base 402. As will be appreciated, the angle $\alpha$ is preferably selected such that the shoulders 404 of adjoining tines in the inner tine layer 210 support the base 402 of a respective tine in the outer layer 208 (seen in FIG. 3). In this manner, the electrode tines of the device 200, when withdrawn into the cannula lumen 203, are nested in offset, circumferential layers having a total radial profile (i.e., height measured radially from the surface of the mandrel 204) that is less than twice the radial height h of an individual tine.

By nesting the electrode tines such that the base 402 of each outer layer tine 208 is resting against the adjacent shoulders of a pair of inner layer tines 210, the overall profile of the respective layers when withdrawn into the cannula is compacted, reducing the total diameter of the device 200 when compared to the total number of electrode tines, without reducing the column strength of the individual tine elements. In alternate embodiments, the respective outer and inner electrode tines 208 and 210 may have different cross-sections and/or be secured to the mandrel 202 in different configurations, which still provide for a relatively low nested profile, i.e., wherein the inner and outer electrode tine layers, when withdrawn into the cannula lumen, have a collective radial height less than twice a maximum radial height h of any one tine.

Figure 5:
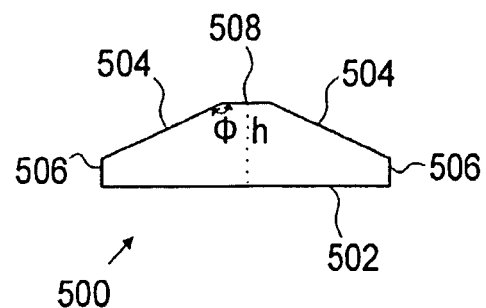
FIG. 5 is a cross-sectional view of an alternate electrode tine for use in further embodiments of the invention.

FIG. 5 illustrates one such alternative cross-sectional profile for an electrode tine 500. In tine 500 includes a substantially flat base 502, substantially orthogonal sides 506, and sloped shoulders 504, similar to the respective base 402, sides 406 and shoulders 404 of tine 400, except that the shoulders 504 do not intersect. Instead, the tine 500 has a flat crown 508 that runs substantially parallel to the base 502, and extends at a substantially identical angle $\Phi$ from the respective shoulders 504. As will be appreciated, the crown 508 further limits the radial height h of the tine 500, without imparting much if any loss in column strength.

Although the foregoing embodiments have been described in some detail for purposes of clarity of understanding, there are many alternative ways of implementing the embodiments shown and the disclosed embodiments are merely illustrative and not restrictive of the possible implementations of the invention.

What is claimed:

1. An electrosurgical device for tissue ablation, comprising:

a delivery cannula having a lumen and an open distal end in communication with the lumen;

a mandrel disposed in the lumen of the delivery cannula, the mandrel being axially moveable relative to the cannula;

a plunger mounted on a proximal end of the mandrel, the plunger being configured for electrical connection to a radiofrequency power generator;

a first set of electrode tines having proximal ends attached to and displaced circumferentially around a distal portion of the mandrel, the first set of electrode tines disposed a first radial position;

a second set of electrode tines having proximal ends attached to and displaced circumferentially around a distal portion of the mandrel, the second set of electrode tines disposed at a second radial position located radially outward with respect to the first radial position; and wherein the second set of electrode tines are centered approximately evenly between a pair of electrode tines of the first set, the second set of electrode tines at least partially overlapping the first set of electrode tines when the first and second set of electrode tines are retracted into the lumen of the delivery cannula.

2. The device of claim 1, wherein the first set of electrode tines are formed by cutting the distal portion of the mandrel.

3. The device of claim 2, wherein the second set of electrode tines are bonded to the mandrel.

4. The device of claim 1, wherein the individual tine elements of the first and second sets of electrode tines have substantially uniform cross-sectional profiles.

5. The device of claim 1, wherein the individual tine elements of the first and second sets of electrode tines have different cross-sectional profiles.

6. The device of claim 1, wherein the proximal ends of the second set of electrode tines extend proximally beyond the proximal ends of the first set of electrode tines.

7. The device of claim 1, wherein the individual tines of the first and second set of electrode tines have an A-frame shape comprising a base, first and second sides extending generally perpendicular with respect to the base, and first and second shoulders extending at substantially identical angles from respective ends of the first and second sides and intersecting at an intersection point.

8. The device of claim 7, wherein, the respective bases of the second set of electrode tines contact respective shoulders of the first set of electrode tines when the first and second set of electrode tines are retracted into the lumen of the delivery cannula.

9. The device of claim 1, wherein the thickness of the overlapping first and second set of electrode tines is less than the sum of the maximal radial thickness of any one electrode tine of the first and second set.

10. The device of claim 1, further comprising a third set of electrode tines having proximal ends attached to and displaced circumferentially around a distal portion of the mandrel, the third set of electrodes disposed at a third radial position located radially outward with respect to the second radial position, wherein the third set of electrode tines are centered approximately evenly between a pair of electrode tines of the second set, the third set of electrode tines at least partially overlapping the second set of electrode tines when the electrode tines are retracted into the lumen of the delivery cannula.

11. An electrosurgical system comprising:
a radiofrequency power generator;
a delivery cannula having a lumen and an open distal end in communication with the lumen;
a pusher member disposed in the lumen of the delivery cannula, the pusher member being axially moveable relative to the cannula;
a plunger mounted on a proximal end of the pusher member, the plunger being configured for electrical connection to the radiofrequency power generator;
a first set of electrode tines having proximal ends attached to and displaced circumferentially around a distal portion of the pusher member, the first set of electrode tines disposed a first radial position;
a second set of electrode tines having proximal ends attached to and displaced circumferentially around a distal portion of the pusher member, the second set of electrode tines disposed at a second radial position located radially outward with respect to the first radial position; and
wherein the second set of electrode tines are nested circumferentially in an offset manner about the first set of electrode tines when the first and second set of electrode tines are retracted into the lumen of the delivery cannula.

12. The system of claim 11, wherein the first and second sets of electrode tines are configured in a monopolar mode.

13. The system of claim 11, wherein the first and second sets of electrode tines are configured in a bipolar mode.

14. The system of claim 11, further comprising an obturator configured to receive the delivery cannula.

15. The system of claim 11, wherein the thickness of the nested first and second sets of electrode tines is less than the sum of the maximal radial thickness of any one electrode tine of the first and second set.

16. The system of claim 11, wherein the individual tine elements of the first and second sets of electrode tines have substantially uniform cross-sectional profiles.

17. The system of claim 11, wherein the individual tine elements of the first and second sets of electrode tines have different cross-sectional profiles.

18. The system of claim 11, wherein the individual tines of the first and second sets of electrode tines have an A-frame shape comprising a base, first and second sides extending generally perpendicular with respect to the base, and first and second shoulders extending at substantially identical angles from respective ends of the first and second sides and intersecting at an intersection point.

19. The system of claim 18, wherein, the respective bases of the second set of electrode tines contact respective shoulders of the first set of electrode tines when the first and second set of electrode tines are retracted into the lumen of the delivery cannula.

* * * * *